US012082970B2

United States Patent
Goodman

(10) Patent No.: US 12,082,970 B2
(45) Date of Patent: Sep. 10, 2024

(54) DEVICES, SYSTEMS, AND METHODS FOR EVALUATING ACUTENESS OF DEEP VEIN THROMBOSIS

(71) Applicant: KONINKLIJKE PHILIPS N.V., Eindhoven (NL)

(72) Inventor: David Goodman, San Diego, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 121 days.

(21) Appl. No.: 16/631,034

(22) PCT Filed: Jul. 19, 2018

(86) PCT No.: PCT/EP2018/069632
§ 371 (c)(1),
(2) Date: Jan. 14, 2020

(87) PCT Pub. No.: WO2019/016317
PCT Pub. Date: Jan. 24, 2019

(65) Prior Publication Data
US 2020/0138404 A1 May 7, 2020

Related U.S. Application Data

(60) Provisional application No. 62/535,600, filed on Jul. 21, 2017.

(51) Int. Cl.
*A61B 8/08* (2006.01)
*A61B 8/00* (2006.01)
(Continued)

(52) U.S. Cl.
CPC .............. *A61B 8/0891* (2013.01); *A61B 8/12* (2013.01); *A61B 8/14* (2013.01); *A61B 8/463* (2013.01); *A61B 8/5223* (2013.01)

(58) Field of Classification Search
CPC ........... A61B 8/0891; A61B 8/12; A61B 8/14; A61B 8/463; A61B 8/5223; A61B 8/00; G16H 50/20
See application file for complete search history.

(56) References Cited

U.S. PATENT DOCUMENTS 3,909,771 A * 9/1975 Pickering ................. A61B 8/10
367/104
2005/0004467 A1 1/2005 Shiina
(Continued)

FOREIGN PATENT DOCUMENTS

| JP | H05184575 A | 7/1993 |
|----|-------------|--------|
| JP | 2013070704 A | 4/2013 |
| WO | 2012092444 A2 | 7/2012 |

OTHER PUBLICATIONS

Bassi et al., Acute on Chronic Venous Thromboembolism on Therapeutic Anticoagulation, Hindawi Publishing Corporation Case Reports in Emergency Medicine vol. 2013, Article ID 295261.*
(Continued)

*Primary Examiner* — Bo Joseph Peng

(57) ABSTRACT

A method for evaluating deep vein thrombosis (DVT) caused by a blood clot formed in a deep vein of a patient is provided. The method includes receiving, at a computing device in communication with an ultrasound imaging device, an ultrasound signal representative of an ultrasound echo reflected from the blood clot, wherein the ultrasound echo is associated with an ultrasound pulse transmitted by the ultrasound imaging device; determining, by the computing device, an acuteness of the blood clot based on a strength of the ultrasound signal; and outputting, to a display in communication with the computing device, a graphical indication of the determined acuteness. In some embodiments, the method further includes transmitting, by use of
(Continued)

the ultrasound imaging device, the ultrasound pulse into the deep vein where the blood clot is positioned.

8 Claims, 14 Drawing Sheets

(51) Int. Cl.
*A61B 8/12* (2006.01)
*A61B 8/14* (2006.01)

(56) References Cited

U.S. PATENT DOCUMENTS

| | | | |
|---|---|---|---|
| 2006/0173308 A1* | 8/2006 | Sasaki | G01S 7/5206 600/437 |
| 2008/0081994 A1* | 4/2008 | Kim | A61B 8/06 600/438 |
| 2008/0269605 A1 | 10/2008 | Nakaya | |
| 2013/0184584 A1* | 7/2013 | Berkey | A61B 8/4444 600/441 |
| 2014/0236118 A1 | 8/2014 | Unser | |
| 2015/0025380 A1* | 1/2015 | Azegami | A61B 8/5223 600/438 |
| 2016/0007947 A1* | 1/2016 | Spencer | A61B 8/0841 600/424 |

OTHER PUBLICATIONS

Zhang et al., Non-invasive Thrombolysis using Histotripsy beyond the "Intrinsic" Threshold (Microtripsy), IEEE Trans Ultrason Ferroelectr Freq Control. Jul. 2015 ; 62(7): 1342-1355.*

H. Nakamura et al., Detection of Venous Emboli Using Doppler Ultrasound, European Journal of Vascular and Endovascular Surgery, vol. 35, Issue 1, 2008, pp. 96-101, ISSN 1078-5884, https://doi.org/10.1016/j.ejvs.2007.07.009.*

Clinical Practice Guideline, The Diagnostic Apporach to Acute Venous Thromboembolism, Am J Respir Crit Care Med vol. 160. pp. 1043-1066, 1999.*

Swanson E., Doppler ultrasound imaging for detection of deep vein thrombosis in plastic surgery outpatients: a prospective controlled study. Aesthet Surg J. Feb. 2015;35(2):204-14. doi: 10.1093/asj/sju052. PMID: 25717121.*

Received Signal Strength—an overview, Big Data, 2016, ScienceDirect, https://www.sciencedirect.com/topics/computer-science/received-signal-strength.*

Ali et al., Signal Processing Overview of Ultrasound Systems for Medical Imaging, White Paper, Nov. 2008.*

International Search Report & Written Opinion of PCT/EP2018/069632, dated Nov. 16, 2018.

Rubin, Jonathan M. et al "Sonographic Elasticity Imaging of Acute and Chronic Deep Venous Thrombosis in Humans", American Institute of Ultrasound in Medicine, vol. 25, No. 9, 2006, pp. 1179-1186.

Tapson, Victor F. et al "The Diagnostic Approach to Acute Venous Thromboembolism: Clinical Practice Guideline". American Journal of Respiratory and Critical Care Medicine, vol. 160, pp. 1043-1066, 1999.

Xie, Hua et al "Staging Deep Venous Thrombosis using Ultrasound Elasticity Imaging: Animal Model", Ultrasound in Medicine and Biology, vol. 30, No. 10, pp. 1385-1396, 2004.

"Venous Thromboembolism (Blood Clots) Data and Statistics", Centers for Disease Control and Prevention, Jun. 22, 2015 , https://www.cdc.gov/ncbddd/dvt/data.html.

* cited by examiner

DEVICES, SYSTEMS, AND METHODS FOR EVALUATING ACUTENESS OF DEEP VEIN THROMBOSIS

TECHNICAL FIELD

The present disclosure relates generally to ultrasound imaging, and in particular, to devices, systems, and methods for evaluating acuteness of deep vein thrombosis using ultrasound imaging devices.

BACKGROUND

Deep vein thrombosis (DVT), also known as venous thromboembolism (VT), occurs when a blood clot (thrombus) forms in a deep vein of a patient's body, usually in legs. Blood clots in deep veins not only restrict blood flow in a patient, but also become dangerous when they break loose and travel through bloodstreams to block the blood flow to the patient's lung, also known as pulmonary embolism (PE). DVT has become more and more prevalent over the years, affecting lives of more and more Americans. Centers for Disease Control and Prevention (the "CDC") has predicted that lives of as many as 900,000 people in the U.S. could be affected one way or another by DVT each year (See Centers for Disease Control and Prevention. Venous Thromboembolism (Blood Clots): Data & Statistics, last updated Jun. 22, 2015, available at https://www.cdc.gov/ncbddd/dvt/data.html). The CDC also estimated that around 60,000 to 100,000 Americans could die of DVT each year (See id.). For people who suffer from PE, there is 25% chance that sudden death is the very first symptom (See id.).

Depending on whether DVT is acute or chronic, doctors devise different treatment plans or strategies. Usually a more aggressive treatment plan/strategy would be adopted if a patient is diagnosed with acute DVT. Traditionally, whether a DVT is acute or chronic is determined by the length of time during which symptoms are present. The standard practice in the field draws the dividing line at around 14 days. If symptoms consistent with DVT have been present for 14 days or less, the DVT would be regarded as acute DVT. If such symptoms have been present for more than 14 days, the DVT would be regarded as chronic DVT. Conventionally, a medical care provider determines how long symptoms have been present by interviewing the patient. A doctor would ask when the patient observes a symptom of DVT for the first time and determine if the onset of the symptom is more than 14 days old. The interview process inherently renders the diagnosis unreliable because a patient may misremember the onset of a symptom. An unreliable diagnosis naturally calls into question a treatment plan hinged thereupon.

Therefore, while conventional methods and apparatuses for determining a treatment strategy for DVT, they have not been entirely satisfactory in every aspect.

SUMMARY

Embodiments of the present disclosure provide devices, systems, methods of evaluating DVT caused by a blood clot formed in a deep vein of a patient. The method includes transmitting an ultrasound pulse into a blood clot, receiving an ultrasound signal representative of an ultrasound echo reflected from the blood clot, determining acuteness of the blood clot based on the strength of the ultrasound signal, and outputting a graphical indication of the determined acuteness of the blood clot. To determine acuteness of the blood clot, the method compares strength of the ultrasound signal to a threshold signal strength. If the strength of the ultrasound signal is below the threshold signal strength, the method determines that the blood clot is acute. Otherwise, the method determines that the blood clot is chronic.

Embodiments of the present disclosure also provide a system for evaluating DVT caused by a blood clot formed in a deep vein of a patient. The system includes a processor in communication with an ultrasound imaging device. The processor receives from the ultrasound imaging device an ultrasound signal representative of an ultrasound echo reflected from the blood clot, determines the acuteness of the blood clot based on strength of the ultrasound signal, and output a graphical indication of the determined acuteness to a display. In some instances, the system includes the ultrasound imaging device and the display.

In one embodiment, a method for evaluating deep vein thrombosis (DVT) caused by a blood clot formed in a deep vein of a patient is provided. The method includes receiving, at a computing device in communication with an ultrasound imaging device, an ultrasound signal representative of an ultrasound echo reflected from the blood clot, wherein the ultrasound echo is associated with an ultrasound pulse transmitted by the ultrasound imaging device; determining, by the computing device, an acuteness of the blood clot based on a strength of the ultrasound signal; and outputting, to a display in communication with the computing device, a graphical indication of the determined acuteness. In some embodiments, the method further includes transmitting, by use of the ultrasound imaging device, the ultrasound pulse into the deep vein where the blood clot is positioned.

In some embodiments, determining the acuteness of the blood clot includes comparing a strength of the ultrasound signal to a threshold signal strength; determining that the blood clot is acute if the ultrasound signal is below the threshold signal strength; and determining that the blood clot is chronic if the ultrasound signal is equal to or above the threshold signal strength. In some instances, the method further includes displaying a grey scale image of the ultrasound signal on the display. In some implementations, displaying the grey scale image of the ultrasound signal includes displaying the grey scale image of the ultrasound signal with a first graphical overlay if the ultrasound signal is below the threshold signal strength; and displaying the grey scale image of the ultrasound signal with a second graphical overlay if the ultrasound signal is equal to or above the threshold signal strength. In some embodiments, the first graphical overlay includes a first color and the second graphical overlay includes a second color different from the first color. In some other embodiments, the first graphical overlay includes a first text and the second graphical overlay includes a second text different from the first text. In some instances, the ultrasound imaging device is an intravascular ultrasound catheter. In other instances, the ultrasound imaging device is an external ultrasound probe.

Embodiments of the present disclosure provide a system for evaluating deep vein thrombosis (DVT) caused by a blood clot formed in a deep vein of a patient. The system includes a processor in communication with an ultrasound imaging device, the processor operable to: receive an ultrasound signal representative of an ultrasound echo reflected from the blood clot, the ultrasound echo associated with an ultrasound pulse transmitted by the ultrasound imaging device; determine, an acuteness of the blood clot based on a strength of the ultrasound signal; and output, to a display, a graphical indication of the determined acuteness. In some implementations, the system includes the ultrasound imaging device. The ultrasound imaging device is configured to transmit the ultrasound pulse into the deep vein where the blood clot is positioned and receive the ultrasound signal representative of the ultrasound echo reflected from the blood clot. In some instances, the processor is operable to compare a strength of the ultrasound signal to a threshold signal strength and determine that the blood clot is acute if the ultrasound signal is below the threshold signal strength. In some implementations, the system further includes the display that is configured to display a grey scale image of the ultrasound signal representative of the ultrasound echo reflected from the blood clot.

In some embodiments, the display of the system displays the grey scale image of the ultrasound signal with a first graphical overlay if the ultrasound signal is below the threshold signal strength; and displays the grey scale image of the ultrasound signal with a second graphical overlay if the ultrasound signal is equal to or above the threshold signal strength. In some instances, the first graphical overlay includes a first color and the second graphical overlay includes a second color different from the first color. In some implementations, the first graphical overlay includes a first text and the second graphical overlay includes a second text different from the first text. In some instances, the ultrasound imaging device is an intravascular ultrasound catheter. In some other instances, ultrasound imaging device is an external ultrasound probe. In one embodiment, ultrasound pulse includes a frequency of 10 MHz. In another embodiment, the ultrasound pulse includes a frequency of 20 MHz.

Other devices, systems, and methods specifically configured to interface with such devices and/or implement such methods are also provided.

Additional aspects, features, and advantages of the present disclosure will become apparent from the following detailed description along with the drawings.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1:
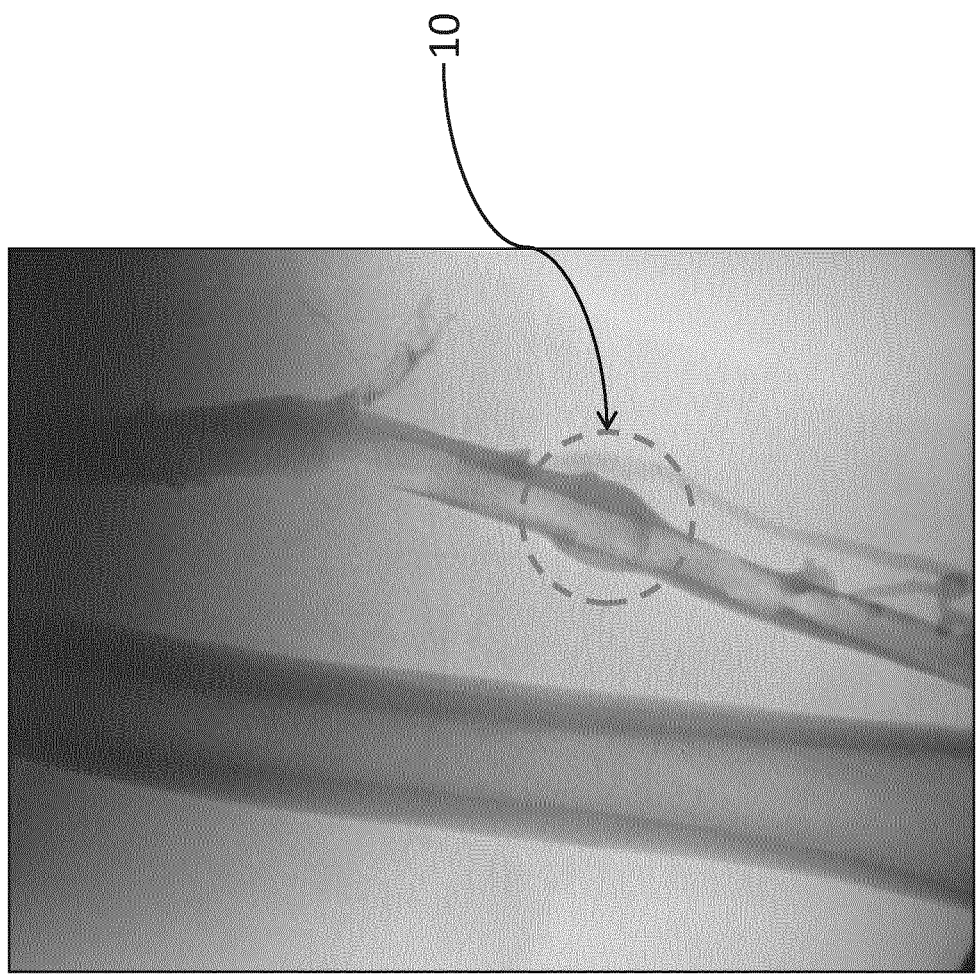
FIG. 1 is an angiographic image of an acute femoral DVT.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, the present disclosure provides an ultrasound imaging system described in terms of cardiovascular imaging, however, it is understood that such description is not intended to be limited to this application, and that such imaging system can be utilized for imaging throughout the body. In some embodiments, the illustrated ultrasound imaging system is a side looking intravascular imaging system, although transducers formed according to the present disclosure can be mounted in other orientations including forward looking. The imaging system is equally well suited to any application requiring imaging within a small cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

DVT is a condition where a blood clot is embedded in one of the major deep veins in the lower legs, thighs, pelvis, or arms. For example, when a blood clot is found embedded in a femoral vein of a patient, the patient would be diagnosed with DVT. A blood clog embedded in a vein can restrict or block blood circulation through the vein, causing pain, swelling, warmth, skin discoloration, and inflammation in the affected limb. There are generally two types of DVT-chronic DVT and acute DVT. Chronic and acute DVT are differentiated based on how long they have existed. While different schools of doctors may have slightly different definitions, usually DVT that has existed for more than 14 days is referred to as chronic DVT and that has not is referred to as acute DVT. Traditionally a doctor would determine how long DVT has existed by enquiring the patient how long symptoms have been felt or observed. For example, if a patient complains about a sharp pain in his/her calf since 10 days ago and certain tests have been done to confirm existence of DVT, the patient is likely to be diagnosed with acute DVT.

Figure 2:
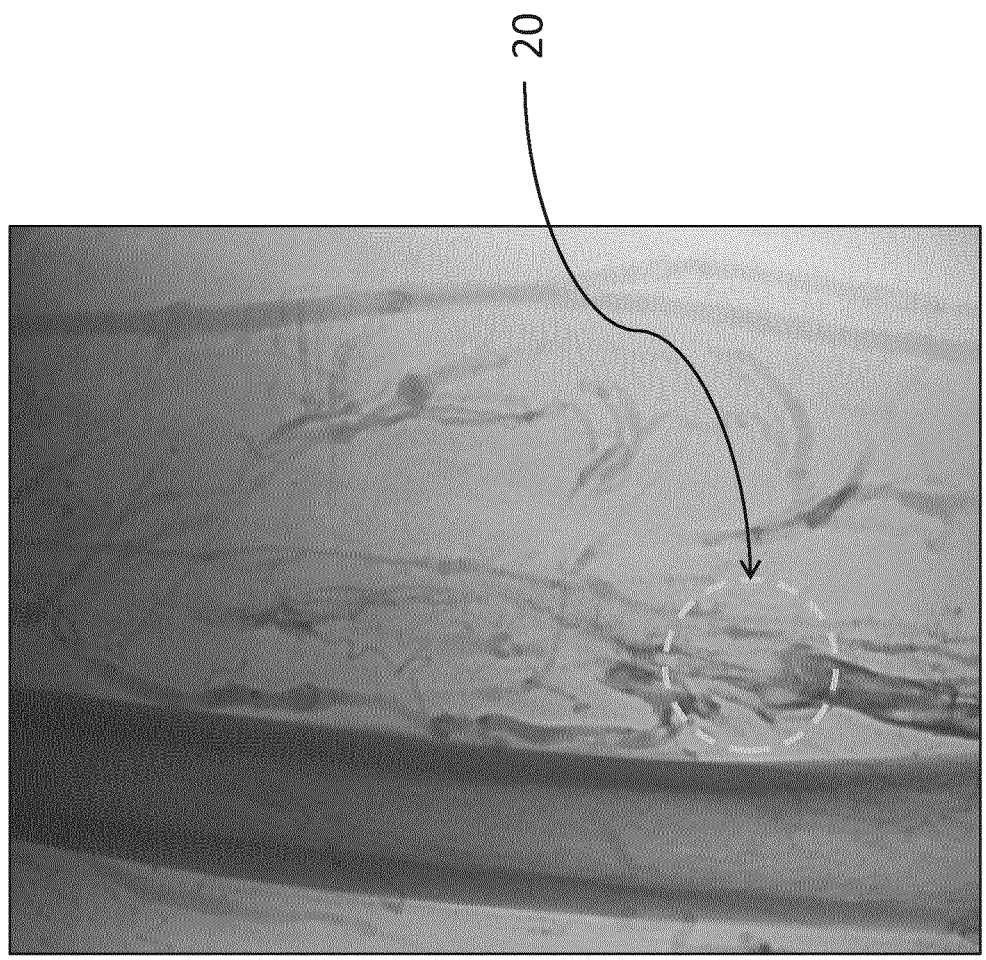
FIG. 2 is an angiographic image of a chronic femoral DVT.

Chronic and acute DVT have been associated with various characteristics. For example, an acute clot has been observed to cause vein dilation, be non-compressible, have smooth borders, and have homogeneous textures. A chronic clot has been observed to decrease vein diameter, cause wall thickening, have rough borders, have heterogeneous textures, and cause blood reflux. References are now made to FIGS. 1 and 2, the former showing an angiographic image of an acute DVT 10 and the latter showing an angiographic image of a chronic DVT 20. As can be seen from them, the acute DVT 10 causes the vein to dilate, has smooth borders, and has homogeneous textures. The chronic DVT 20 has rough borders and heterogeneous textures. While acute DVT and chronic DVT have these different features, sometimes they are not reliable indicators of acuteness of DVT. That is the reason why acuteness is usually determined by interviewing the patient.

Chronic DVT and acute DVT are treated differently. When a blood clot is allowed to mature for more than 14 days, the blood clot becomes harder and its internal structure becomes more organized, making it difficult to dissolve. In most cases, chronic DVT scars the vein and is not susceptible to removal by administration of drugs. This results in distinctive treatment plans for chronic DVT and acute DVT. Oftentimes when a patient is diagnosed with acute DVT, treatment options would include administration of anticoagulants and clot-busters. Anticoagulants, sometimes referred to as blood thinners, prevent blood from clotting, thus preventing blood clots from getting bigger and breaking loose. Examples include heparin, enoxaparin, dalteparin, fondaparinux injections and warfarin and rivaroxaban pills. Different from blood thinners, clot-busters, such as tissue plasminogen activators (tPA), can be administrated to break up an acute blood clot in life-threatening situations. In addition, because acute blood clots are softer and tend to break loose, sometimes filters can be inserted into a large vein to catch any acute blood clots flowing toward a patient's vital organs. Anticoagulants and clot-busters are not effective treatments for chronic DVT. Also, because a chronic blood clot usually does not break loose, doctors would not recommend insertion of any filters to catch free-flowing blood clot. When a chronic blood clot blocks a patient's blood flow, doctors usually have to adopt invasive treatments to open up the blood flow. These invasive treatments include use of stents. As can be appreciated from the foregoing descriptions, determination of acuteness of DVT really is the bifurcation point of DVT treatment. The treatment either goes down the chronic DVT route or the acute DVT route.

Figure 3:
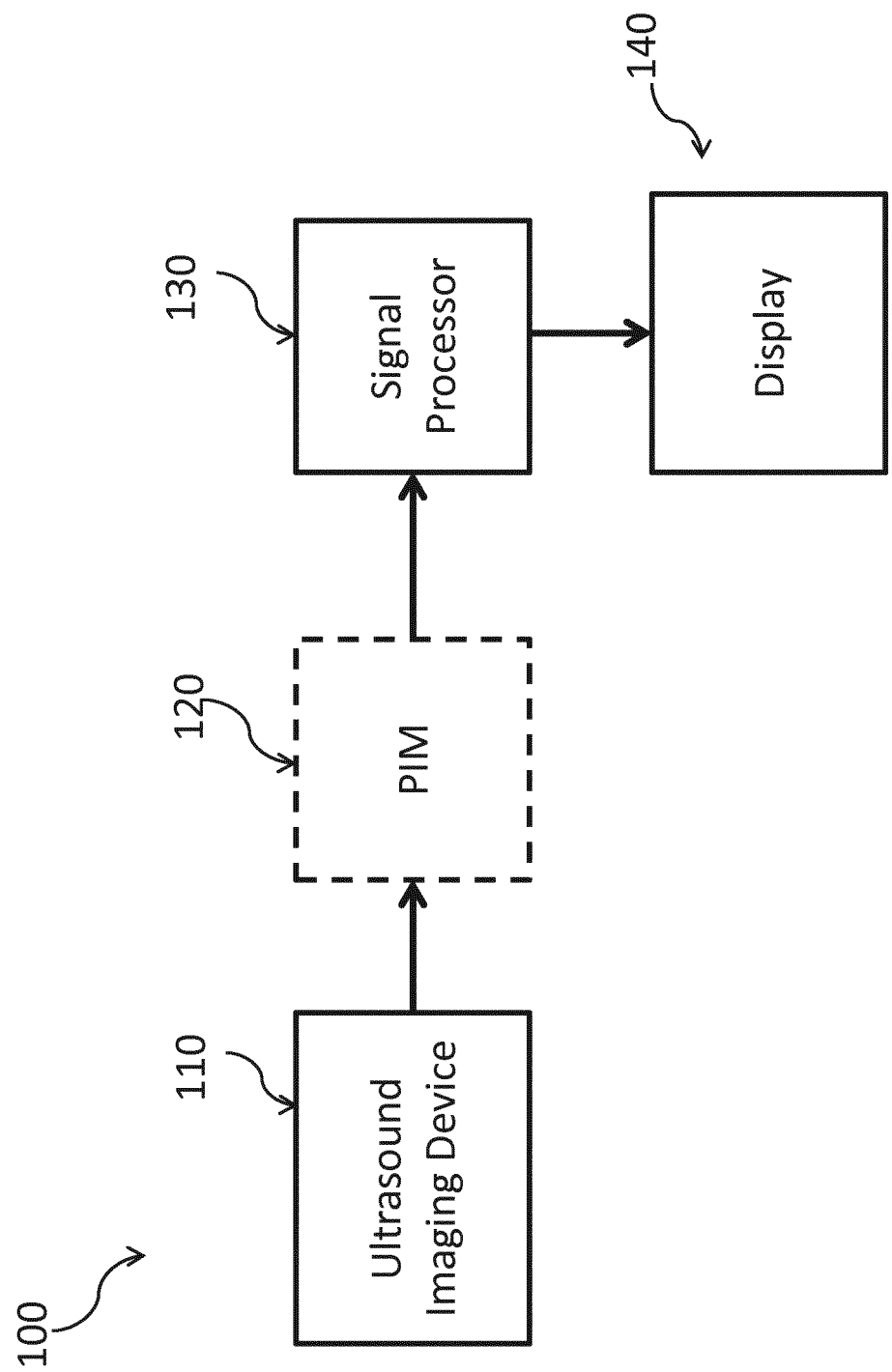
FIG. 3 is a schematic diagram of a system for evaluating acuteness of DVT, according to aspects of the present disclosure.

FIG. 3 is a schematic diagram of a system 100 for evaluating acuteness of DVT, according to aspects of the present disclosure. System 100 includes an ultrasound imaging device 110, a patient interface module (PIM) 120, a signal processor 130, and a display 140. In some instances, the ultrasound imaging device 110 transmits an ultrasound pulse to a deep vein where a blood clot is positioned. Once the ultrasound pulse reaches the blood clot, the blood clot reflects an ultrasound echo back to the ultrasound imaging device 110 in the form of an ultrasound signal. The ultrasound imaging device 110 receives the ultrasound signal and passes the ultrasound signal to the signal processor 130 through the PIM 120. In some instances, the ultrasound imaging device 110 can directly interface the signal processor 130. In those instances, the system 100 does not include a PIM 120. In some embodiments, the signal processor 130 determines the acuteness of the blood clot based on the ultrasound signal from the ultrasound imaging device 110. In some instances, the signal processor 130 processes the received ultrasound signal to evaluate the acuteness of the blood clot. In some instances, the signal processor 130 compares the received ultrasound signal with a threshold signal strength. When the strength of the ultrasound signal is below the threshold signal strength, the signal processor 130 would determine that the blood clot is acute. When the strength of the ultrasound signal is equal to or above the threshold signal strength, the signal processor 130 would determine that the blood clot is chronic. In some embodiments, the system 100 is in communication with a display 140 and outputs a graphical indication of the determined acuteness of the blood clot. In some instances, the display 140 is configured to display a grey scale image of the ultrasound signal received by the ultrasound imaging device 110.

In some instances, a graphical indication includes graphical overlays of different colors for chronic DVT and acute DVT. For example, an acute DVT can be shown with a red graphical overlay and a chronic DVT can be shown with a green graphical overlay. Thus, the acuteness of DVT and its distribution within a deep vein can be readily shown and differentiated. In some other instances, a graphical indication includes graphical overlays of different texts for chronic DVT and acute DVT. For example, an acute blood clot can be shown with a text "potential acute DVT identified" or a chronic blood clot can be shown with a text "potential chronic DVT identified."

Figure 4:
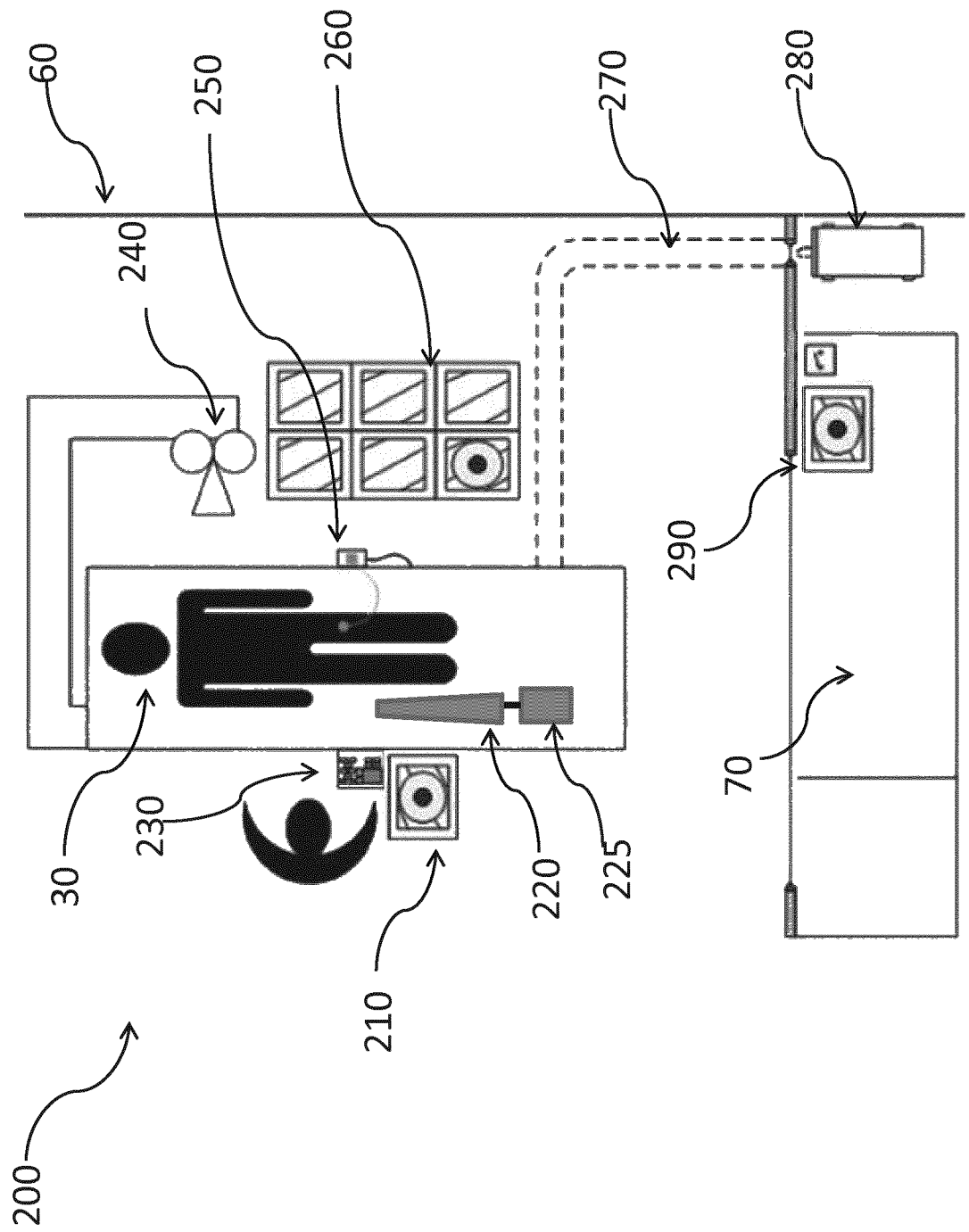
FIG. 4 is a schematic diagram of an exemplary system for evaluating acuteness of DVT, according to aspects of the present disclosure.

FIG. 4 is a schematic diagram of a system 200 for evaluating acuteness of DVT, according to aspects of the present disclosure. The system 200 is an integrated system for acquisition, control, interpretation, and display of ultrasound data. In some embodiment, the system 200 includes a computer system 280 with the hardware and software to acquire, process, and display ultrasound signals, but, in other embodiments, the computer system 280 includes any other type of computing system operable to process ultrasound data. In the embodiments in which the computer system 280 includes a computer workstation, the computer system 280 includes a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and/or a network communication device such as an Ethernet controller and/or wireless communication controller. In that regard, in some particular instances, the computer system 280 is programmed to execute steps associated with the data acquisition and analysis described herein. Accordingly, it is understood that any steps related to data acquisition, data processing, instrument control, and/or other processing or control aspects of the present disclosure may be implemented by the computer system 280 using corresponding instructions stored on or in a non-transitory computer readable medium accessible by the processing system. In some instances, the computer system 280 is portable (e.g., handheld, on a rolling cart, etc.). Further, it is understood that in some instances, computer system 280 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

In the illustrated embodiment, the system 200 is deployed in a catheter lab 60 having a control room 70, with the computer system 280 being located in the control room 70. In other embodiments, the computer system 280 may be located elsewhere, such as in the catheter lab 60, in a centralized area in a medical facility, or at an off-site location accessible over a network. For example, the computer system 280 may be a cloud-based resource. The catheter lab 60 includes a sterile field generally encompassing a procedure area, whereas the associated control room 70 may or may not be sterile depending on the requirements of a procedure and/or health care facility. The catheter lab 60 and control room 70 may be used to perform on a patient 30 any number of medical sensing procedures such as angiography, intravascular ultrasound (IVUS), photoacoustic IVUS, forward looking IVUS (FL-IVUS), virtual histology (VH), intravascular photoacoustic (IVPA) imaging, pressure determination, optical pressure determination, a fractional flow reserve (FFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. Further, the catheter lab 60 and control room 70 may be used to perform one or more treatment or therapy procedures on a patient such as radiofrequency ablation (RFA), cryotherapy, atherectomy or any other medical treatment procedure known in the art. In some instances, the catheter lab 60 includes a plurality of medical instruments including medical sensing devices that collect medical sensing data in various different medical sensing modalities from the patient 30.

In some embodiments, the ultrasound imaging device 220 is an IVUS catheter. The IVUS catheter 220 can include a flexible elongate member sized and shaped for insertion into the vasculature of the patient. An ultrasound transducer or array of ultrasound transducers can be disposed at a distal portion of the flexible elongate member. The IVUS catheter can be positioned within the vasculature and obtain ultrasound imaging data while positioned within the vasculature. A proximal portion of the flexible elongate member can be mechanically and/or electrically coupled to the PIM in some embodiments. In various embodiments, the IVUS catheter 220 can be in wired or wireless communication with the PIM (e.g., PIM 120) and/or a computing device (e.g., the signal processor 130).

The IVUS catheter 220 can be a solid-state catheter or a rotational catheter. An exemplary solid-state catheter uses an array of transducers distributed around a circumference of the catheter and connected to an electronic multiplexer circuit. The multiplexer circuit selects transducers from the array for transmitting ultrasound signals and receiving reflected ultrasound signals. By stepping through a sequence of transmit-receive transducer pairs, the solid-state catheter can synthesize the effect of a mechanically scanned transducer element, but without moving parts. Since there is no rotating mechanical element, the transducer array can be placed in direct contact with blood and vessel tissue with minimal risk of vessel trauma, and the solid-state scanner can be wired directly to the imaging system with a simple electrical cable and a standard detachable electrical connector. Sometimes a solid-state catheter is referred to as a phased-array catheter. An exemplary rotational catheter includes a single transducer located at a tip of a flexible driveshaft that spins inside a sheath inserted into the vessel of interest. The transducer is typically oriented such that the ultrasound signals propagate generally perpendicular to an axis of the catheter. In the typical rotational catheter, a fluid-filled (e.g., saline-filled) sheath protects the vessel tissue from the spinning transducer and driveshaft while permitting ultrasound signals to freely propagate from the transducer into the tissue and back. As the driveshaft rotates (for example, at 30 revolutions per second), the transducer is periodically excited with a high voltage pulse to emit a short burst of ultrasound. The ultrasound signals are emitted from the transducer, through the fluid-filled sheath and sheath wall, in a direction generally perpendicular to an axis of rotation of the driveshaft. The same transducer then listens for returning ultrasound signals reflected from various tissue structures, and the imaging system assembles a two dimensional image of the vessel cross-section from a sequence of several hundred of these ultrasound pulse/echo acquisition sequences occurring during a single revolution of the transducer. In some instances, the ultrasound imaging device 220 operates at a frequency of 10 MHz or 20 MHz. The ultrasound imaging device 220 operating at 10 MHz penetrates deeper in human tissues and has a larger field of view. The ultrasound imaging device 220 operating at 20 MHz does not penetrate as deep but generates grey scale images of higher resolutions.

In some instances, an IVUS patient interface module (PIM) 225 couples the IVUS catheter 220 to the computer system 280 through connection 270. In particular, the IVUS PIM 225 is operable to receive ultrasound signals collected from the patient 30 by the IVUS catheter 220, and is operable to transmit the received ultrasound signals to the computer system 280 in the control room 70. In one embodiment, the PIM 225 includes analog to digital (A/D) converters and transmits digital data to the computer system 280, however, in other embodiments, the PIM 225 transmits analog data to the computer system 280. In one embodiment, the IVUS PIM 225 transmits the ultrasound signals over a Peripheral Component Interconnect Express (PCIe) data bus connection, but, in other embodiments, it may transmit data over a USB connection, a Thunderbolt connection, a FireWire connection, or some other high-speed data bus connection. In other instances, the IVUS PIM 225 may be connected to the computer system 280 via wireless connections using IEEE 802.11 Wi-Fi standards, Ultra Wide-Band (UWB) standards, wireless FireWire, wireless USB, or another high-speed wireless networking standard. In some instances, to determine if a blood clot is acute or chronic, the computer system 280 compares the received ultrasound signal with a threshold signal strength. The threshold signal strength can a fixed or an adjustable value stored in the computer system 280. In the latter case, the value is adjusted based on test results of the patient or clinical history of the patient. When the strength of the ultrasound signal is below the threshold signal strength, the computer system 280 would determine that the blood clot is acute. When the strength of the ultrasound signal is equal to or above the threshold signal strength, the computer system 280 would determine that the blood clot is chronic. After the computer system 280 determines the acuteness of the blood clot, in some embodiments, the computer system 280 is operable to output a graphical indication of the determined acuteness of the blood clot to a display, such as one of the monitors of the boom display 260.

Additionally, in the system 200, an electrocardiogram (ECG) device 250 is operable to transmit electrocardiogram signals or other hemodynamic data from patient 30 to the computer system 280. Further, an angiogram system 240 is operable to collect x-ray, computed tomography (CT), or magnetic resonance images (MRI) of the patient 30 and transmit them to the computer system 280. In one embodiment, the angiogram system 240 is communicatively coupled to the computer system 280 through an adapter device. Such an adaptor device may transform data from a proprietary third-party format into a format usable by the computer system 280. In some embodiments, the computer system 280 is operable to co-register image data from angiogram system 240 (e.g., x-ray data, MRI data, CT data, etc.) with ultrasound signals from the IVUS catheter 220. As one aspect of this, the co-registration may be performed to generate three-dimensional images with the sensing data.

A bedside controller 210 is also communicatively coupled to the computer system 280 and provides user control of the particular medical modality (or modalities) being used to diagnose the patient 30. In some embodiments, the bedside controller 210 is a touch screen controller that provides user controls and diagnostic images on a single surface. In alternative embodiments, however, the bedside controller 210 may include both a non-interactive display and separate controls, such as physical buttons and/or a joystick, arranged on a control panel 230.

A main controller 290 in the control room 70 is also communicatively coupled to the computer system 280 and, as shown in FIG. 4, is adjacent to catheter lab 60. In the current embodiment, the main controller 290 is similar to the bedside controller 210 in that it includes a touch screen and is operable to display a multitude of GUI-based workflows corresponding to different medical sensing modalities via a UI framework service executing thereon. In some embodiments, the main controller 290 is used to simultaneously carry out a different aspect of a procedure's workflow than the bedside controller 210. In alternative embodiments, the main controller 290 includes a non-interactive display and standalone controls such as a mouse and keyboard.

The system 200 further includes a boom display 260 communicatively coupled to the computer system 280. The boom display 260 may include an array of monitors, each capable of displaying different information associated with a medical sensing procedure. For example, during an IVUS procedure, one monitor in the boom display 260 may display a tomographic view and one monitor may display a sagittal view.

Additionally, in the illustrated embodiment, medical sensing tools in system 200 discussed above are shown as communicatively coupled to the computer system 280 via a wired connection such as a standard copper link or a fiber optic link, but, in alternative embodiments, the tools may be connected to the computer system 280 via wireless connections using IEEE 802.11 Wi-Fi standards, Ultra Wide-Band (UWB) standards, wireless FireWire, wireless USB, or another high-speed wireless networking standard.

Figure 5:
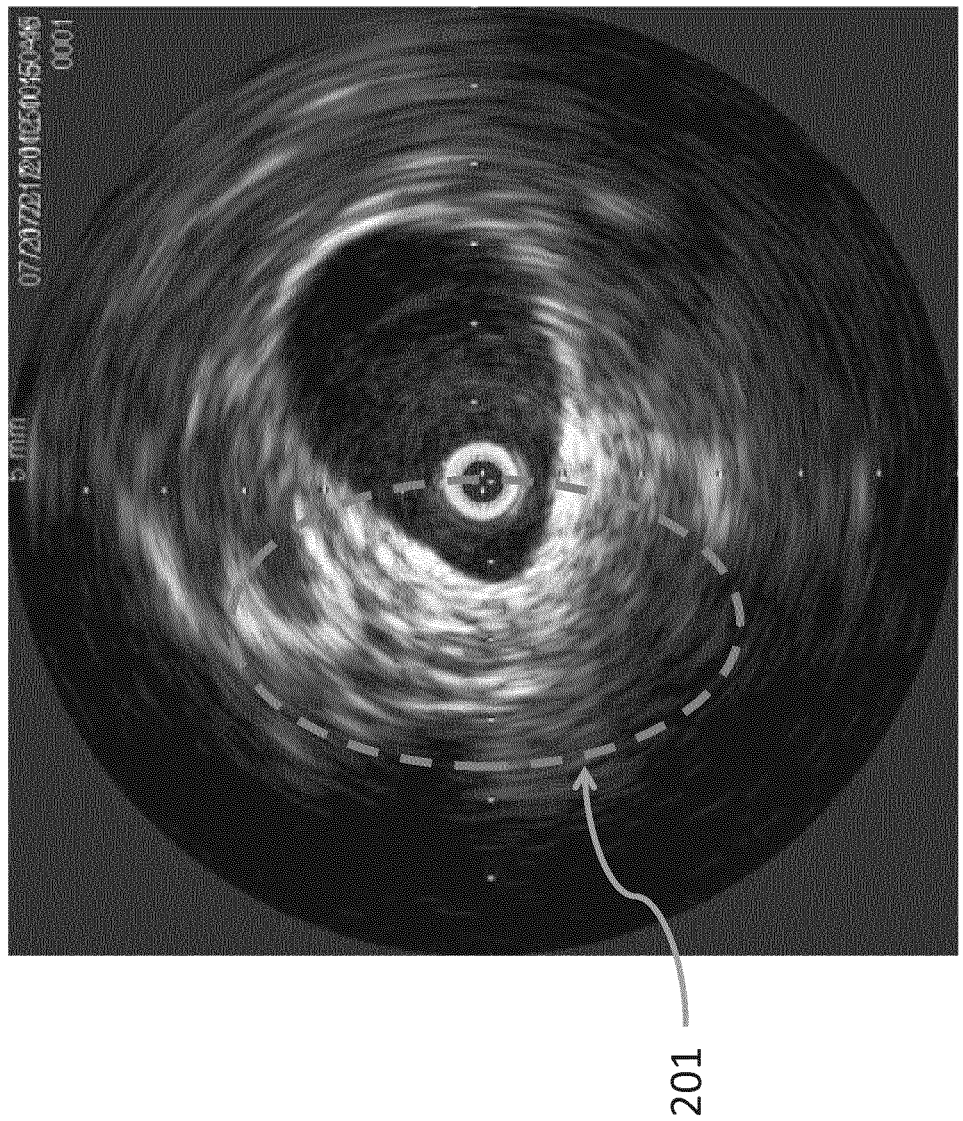
FIG. 5 is an ultrasound grey scale image of chronic DVT taken using an exemplary system, according to aspects of the present disclosure.

Shown in FIG. 5 is an ultrasound grey scale image of chronic DVT taken using the system 200 in FIG. 4, according to aspects of the present disclosure. To take a grey scale image shown in FIG. 5, an IVUS catheter 220 is inserted into a deep vein where a blood clot is positioned. In some instances, the grey image is taken while the IVUS catheter 220 is being pulled back from a distal starting position. The strength of the ultrasound signal representative the ultrasound echo reflected from a blood clot is proportional to the brightness of the grey scale image. That is, the stronger the ultrasound signal is, the brighter the grey scale image will be. A region 201 in the ultrasound grey scale image shown in FIG. 5 contains bright grey scale image signals, indicating a strong reflection of ultrasound echo from the corresponding region in the vein. As discussed above, acute blood clots are softer and echolucent while chronic blood clots are more organized and echogenic. The intense bright grey scale image signals in region 201 therefore indicate presence of chronic blood clots.

Figure 6:
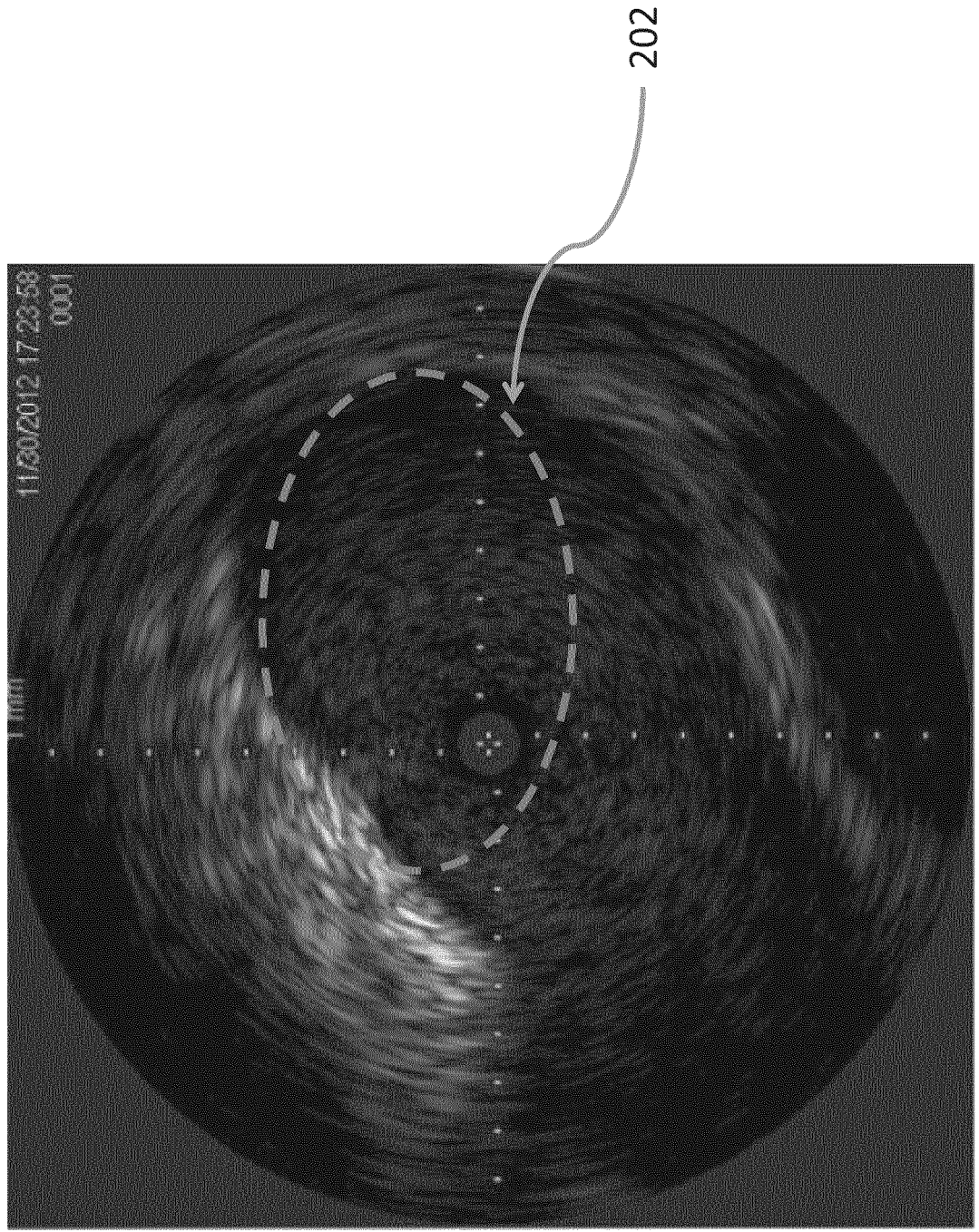
FIG. 6 is an ultrasound grey scale image of acute DVT taken using an exemplary system, according to aspects of the present disclosure.

FIG. 6 is an ultrasound grey scale image of acute DVT taken using the system 200 in FIG. 4, according to aspects of the present disclosure. A region 202 in the ultrasound grey scale image shown in FIG. 6 contain airy low-intensity grey scale image signals, indicating a weak reflection of ultrasound echo from the corresponding region in the vein. The airy low-intensity grey scale image signals in region 202 therefore indicate presence of acute blood clots.

Figure 7:
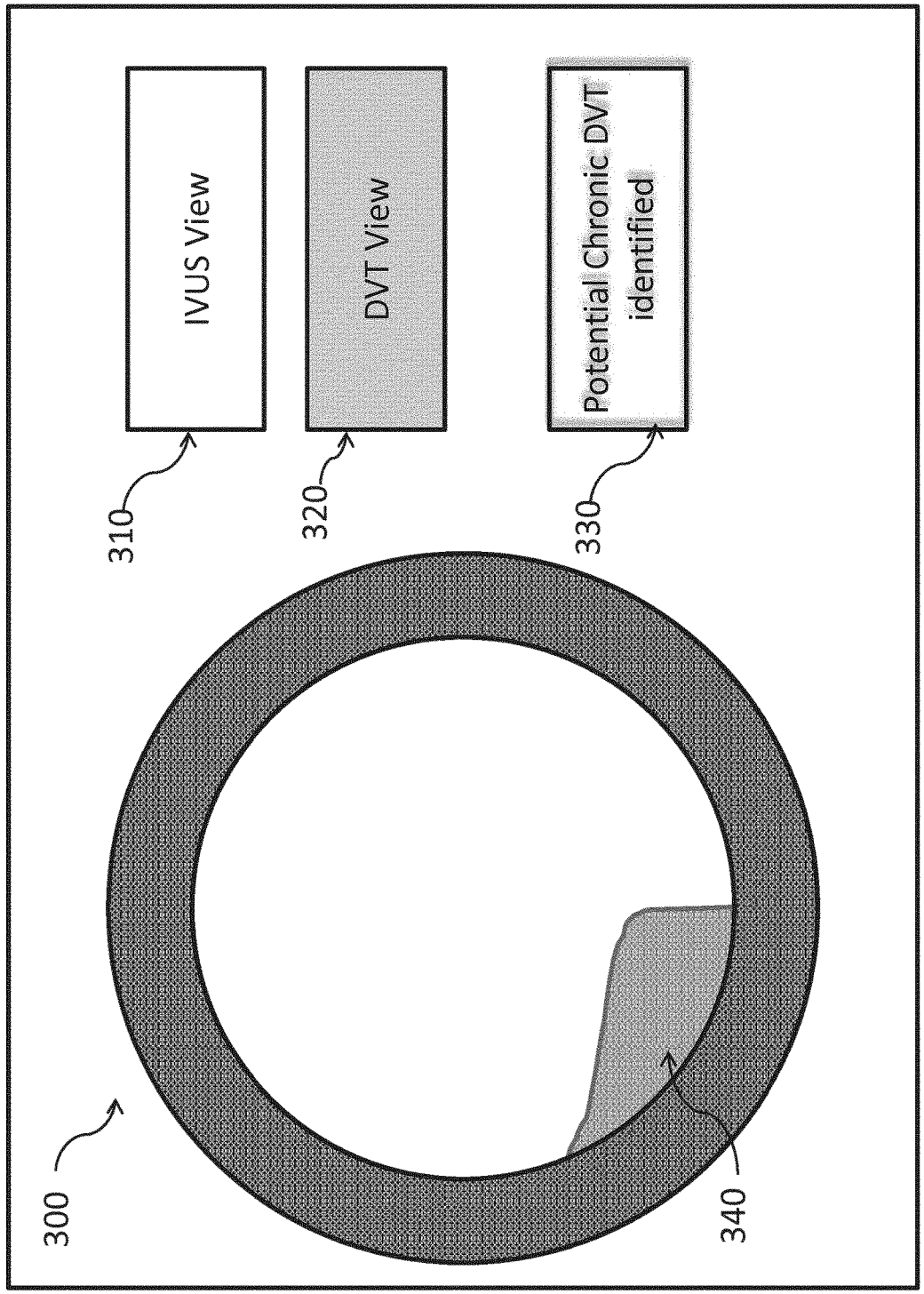
FIG. 7 is a schematic view of a graphic user interface showing identification of chronic DVT, according to aspects of the present disclosure.
Figure 8:
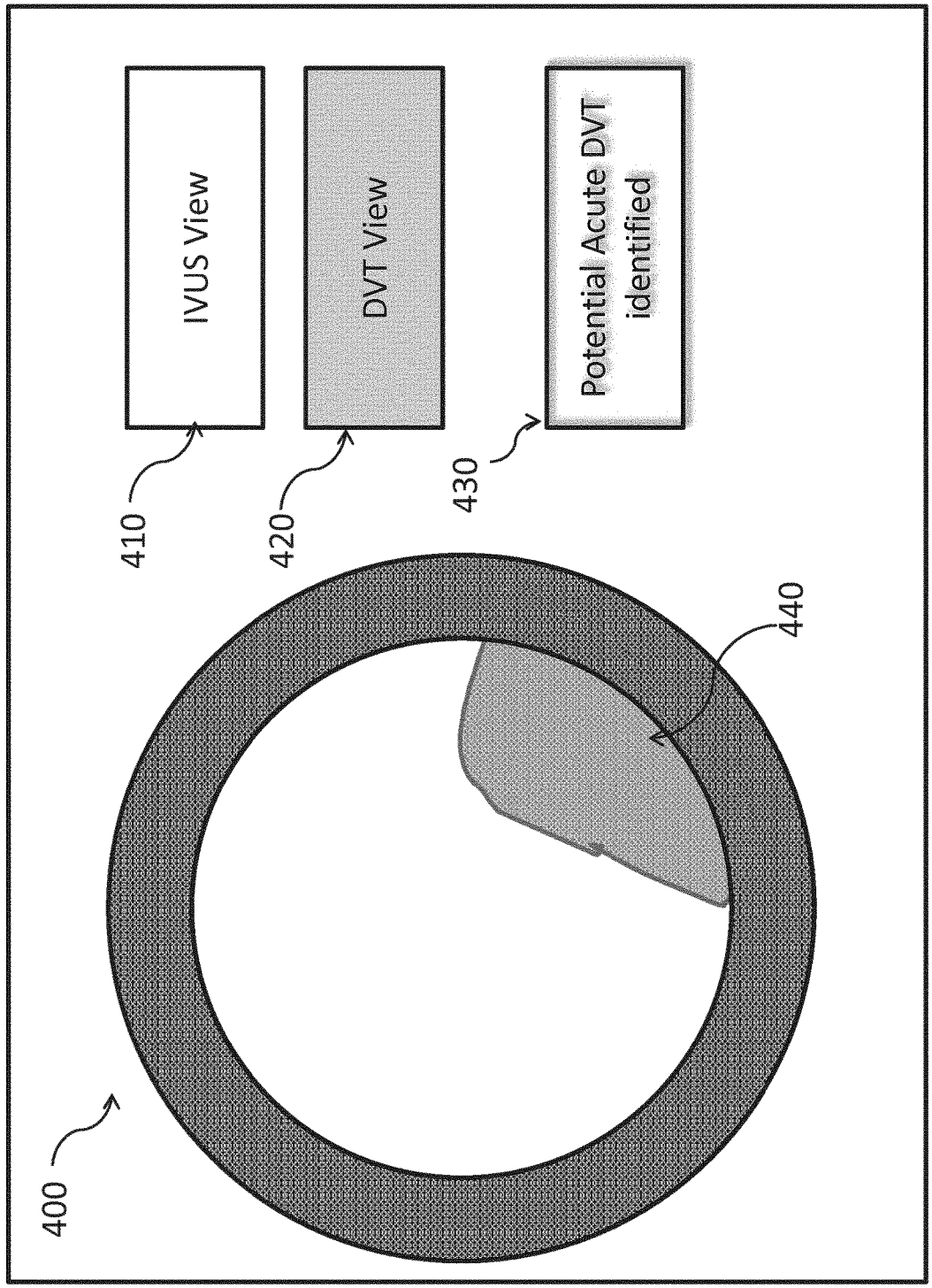
FIG. 8 is a schematic view of a graphic user interface showing identification of acute DVT, according to aspects of the present disclosure.

In some embodiments shown in FIGS. 7 and 8, the boom display 260 includes a graphic user interface showing grey scale images taken by the ultrasound imaging device (IVUS catheter) 220. In some instances, the graphic user interface also displays a selected mode of the system 200 and a graphical indication of the identified acuteness of the blood clot. FIG. 7 is a schematic view of a graphic user interface 300 showing identification of chronic DVT, according to aspects of the present disclosure. In some embodiments, the graphic user interface 300 includes an IVUS view indicator 310, a DVT view indicator 320, an acuteness indicator 330, and a grey scale image taken by the ultrasound imaging device 220. In instances where the IVUS view is selected, the IVUS view indicator 310 is lit or otherwise shown as being selected while the DVT view indicator 320 is shown as being deselected. The instances where the DVT view is selected, the DVT view indicator 320 would appear selected and the IVUS view indicator 310 would appear deselected. In some instances, when the DVT view is selected, a graphical overlay is superimposed onto the grey scale image to better show the acuteness of the blood clot. For example, FIG. 7 illustrates a situation where the DVT view is selected and a blue-colored graphical overlay is superimposed onto the grey scale image in the area 340, indicating that area 340 is likely to be a chronic blood clot. In some instances, the graphic user interface 300 also includes an acuteness indicator 330 to identify acuteness by textual representations. For example, FIG. 7 shows that the acuteness indicator 330 shows "Potential Chronic DVT identified" to communicate the system's evaluation of the acuteness of the blood clot.

FIG. 8 is a photographic image of a graphic user interface 400 showing identification of acute DVT, according to aspects of the present disclosure. In some embodiments, the graphic user interface 400 includes an IVUS view indicator 410, a DVT view indicator 420, an acuteness indicator 430, and a grey scale image taken by the ultrasound imaging device 220. In instances where the IVUS view is selected, the IVUS view indicator 410 is lit or otherwise shown as being selected while the DVT view indicator 420 is shown as being deselected. The instances where the DVT view is selected, the DVT view indicator 420 would appear selected and the IVUS view indicator 410 would appear deselected. In some instances, when the DVT view is selected, a graphical overlay is superimposed onto the grey scale image to better show the acuteness of the blood clot. For example, FIG. 8 illustrates a situation where the DVT view is selected and a red-colored graphical overlay is superimposed onto the grey scale image in the area 440, indicating that area 440 is likely to be an acute blood clot. In some instances, the graphic user interface 400 also includes an acuteness indicator 430 to identify acuteness by textual representations. For example, FIG. 8 shows that the acuteness indicator 430 shows "Potential Acute DVT identified" to communicate the system's evaluation of the acuteness of the blood clot.

Figure 9:
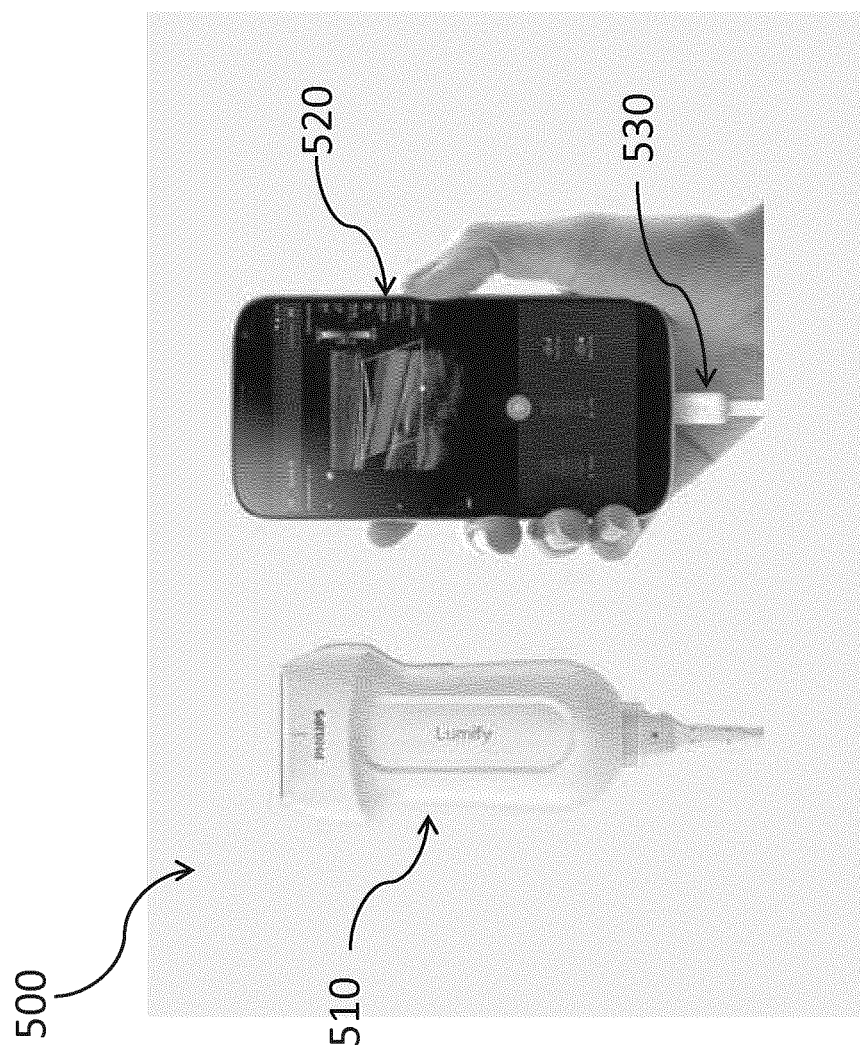
FIG. 9 is a photographic image of another exemplary system for evaluating acuteness of DVT, according to aspects of the present disclosure.

FIG. 9 is a photographic image a system 500 for evaluating acuteness of DVT, according to aspects of the present disclosure. The system 500 includes an ultrasound imaging device 510, a computer system 520, and an adaptor 530. In some embodiments, the ultrasound imaging device 510 is an external ultrasound probe. In some instances, the ultrasound imaging device 510 is fully immersible or at least partially waterproof. An external ultrasound probe is used with an ultrasound transmission gel. An ultrasound transmission gel is first applied to a limb of a patient where the deep vein blood clot is positioned, the external ultrasound probe is then put in contact with the patient's limb for ultrasonic imaging. In some instances, the ultrasound imaging device 510 transmits an ultrasound pulse to a blood clot in a deep vein of a patient. The blood clot reflects an ultrasound echo back to the ultrasound imaging device 510 in the form of an ultrasound signal. In some instances, the ultrasound imaging device 510 operates at a frequency of 10 MHz or 20 MHz. The ultrasound imaging device 510 operating at 10 MHz penetrates deeper in human tissues and has a larger field of view. The ultrasound imaging device 510 operating at 20 MHz does not penetrate as deep but generates grey scale images of higher resolutions.

The ultrasound imaging device 510 then passes the ultrasound signal to the computer system 520 through connection to the computer system 520 via the adaptor. In some instances, the computer system 520 is a portable computing device, such as a tablet personal computer, a laptop computer, a cellphone, or a specialized handheld device. In some embodiments, the computer system 520 includes a display to display a graphical indication of acuteness of the blood clot. In some embodiments, the display of the computer system 520 displays a grey scale image of the ultrasound signal. In some embodiments, the computer system 520 includes a processor operable to receive the ultrasound signal representative of the ultrasound echo reflected from the blood clot and determine acuteness of the blood clot based on the strength of the ultrasound signal. In some instances, the processor is also operable to output a graphical indication of the determined acuteness to the display of the computer system 520. In some instances, to determine if a blood clot is acute or chronic, the computer system 520 compares the received ultrasound signal with a threshold signal strength. The threshold signal strength can a fixed or an adjustable value stored in the computer system 520. In the latter case, the value is adjusted based on test results of the patient or clinical history of the patient. When the strength of the ultrasound signal is below the threshold signal strength, the computer system 520 would determine that the blood clot is acute. When the strength of the ultrasound signal is equal to or above the threshold signal strength, the computer system 520 would determine that the blood clot is chronic. A threshold may be set in the interval of +3 to +6 dB compared to the intensity of the background blood speckle at the ultrasound imaging frequency, with a threshold around +6 dB generally resulting in good discrimination between acute and chronic blood clot, however the threshold value can be adjusted based on test results of the patient or clinical history of the patient. For higher ultrasound imaging frequencies the intensity of the background blood speckle increases, which may result in a finer tuning of the threshold value in the interval of about +3 to +6 dB, therefore a threshold value set for imaging at 10 MHz may be different than for imaging at 20 MHz. The threshold value may be expressed as the intensity of the pixels in the region of interest for a blood clot to be qualified in an ultrasound image, with respect to the intensity of the pixels of a region representing blood speckle at the ultrasound imaging frequency. The threshold value in dB can be converted to a threshold value in intensity of pixels.

In some embodiments, the system 500 includes a Doppler ultrasound modality. In the Doppler ultrasound modality, the ultrasound imaging device 510 transmits ultrasound pulses to the blood flowing through the vein and receives ultrasound echo reflected from the flowing blood. The changes in pitches of the reflected ultrasound due to the Doppler effect can be used to measure the blood flow rate in the vein.

Similar to the graphic user interfaces shown in FIGS. 7 and 8, in some instances, the system 500 can have a graphic user interface, most likely on the display of the computer system 520. The graphic user interface shows grey scale images taken by the ultrasound imaging device (external ultrasound) 510. In some instances, the graphic user interface also displays a selected mode of the system 500 and a graphical indication of the identified acuteness of the blood clot. In some embodiments, the graphic user interface of the system 500 includes an external ultrasound view indicator, a DVT view indicator, an acuteness indicator, and a grey scale image taken by the ultrasound imaging device 510. In instances where the IVUS view is selected, the IVUS view indicator is lit or otherwise shown as being selected while the DVT view indicator is shown as being deselected. In instances where the DVT view is selected, the DVT indicator would appear selected and the IVUS view indicator would appear deselected. In some instances, when the DVT view is selected, a graphical overlay is superimposed onto the grey scale image to better show the acuteness of the blood clot. For example, a graphical overlay of a first color can be superimposed onto the grey scale image in an area to indicate a potential chronic blood clot and a graphical overlay of a second color can be superimposed onto the grey scale image in another area to indicate a potential acute blood clot. In some instances, the first color is different from the second color. In some instances, the graphic user interface of the system 500 also includes an acuteness indicator to identify acuteness by textual representations. In some embodiments, the acuteness indicator of system 500 shows "Potential Chronic DVT identified" or "Potential Acute DVT identified" to communicate the system's evaluation of the acuteness of the blood clot. In some embodiments, the graphic user interface of the system 500 can further include a Doppler ultrasound view indicator. When the Doppler ultrasound view is selected, the Doppler ultrasound view indicator would appear selected and the display of the computer system 520 would display color Doppler ultrasound images, similar to those shown in FIGS. 10 and 11.

Figure 10:
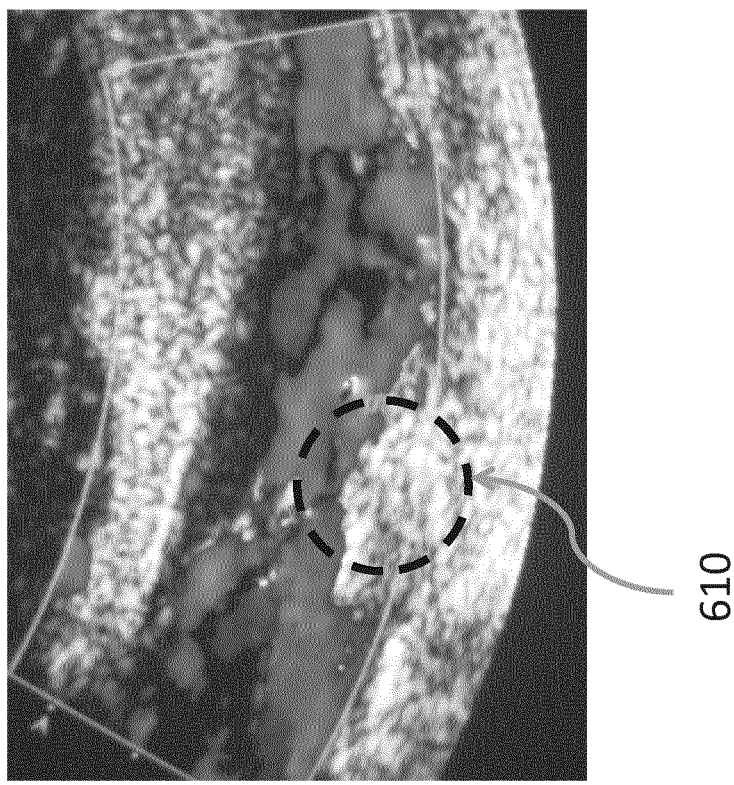
FIG. 10 is an ultrasound grey scale image of chronic DVT taken using an example system, according to aspects of the present disclosure.

Shown in FIG. 10 is an ultrasound grey scale image of chronic DVT taken using the system 500, according to aspects of the present disclosure. The strength of the ultrasound signal representative the ultrasound echo reflected from a blood clot is proportional to the brightness of the grey scale image. That is, the stronger the ultrasound signal is, the brighter the grey scale image will be. A region 610 in the ultrasound grey scale image shown in FIG. 10 contains bright grey scale image signals, indicating a strong reflection of ultrasound echo from the corresponding region in the vein. As discussed above, acute blood clots are softer and echolucent while chronic blood clots are more organized and echogenic. The intense bright grey scale image signals in region 610 therefore indicate presence of chronic blood clots.

Figure 11:
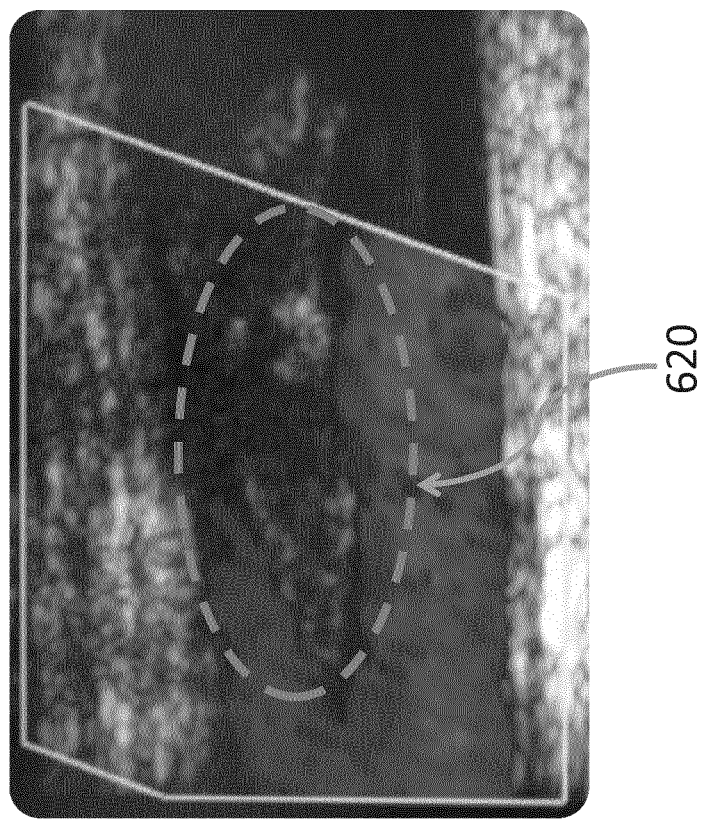
FIG. 11 is an ultrasound grey scale image of acute DVT taken using an example system, according to aspects of the present disclosure.

Shown in FIG. 11 is an ultrasound grey scale image of acute DVT taken using system 500, according to aspects of the present disclosure. A region 620 in the ultrasound grey scale image shown in FIG. 11 contain airy low-intensity grey scale image signals, indicating a weak reflection of ultrasound echo from the corresponding region in the vein. The airy low-intensity grey scale image signals in region 620 therefore indicate presence of acute blood clots.

Figure 12:
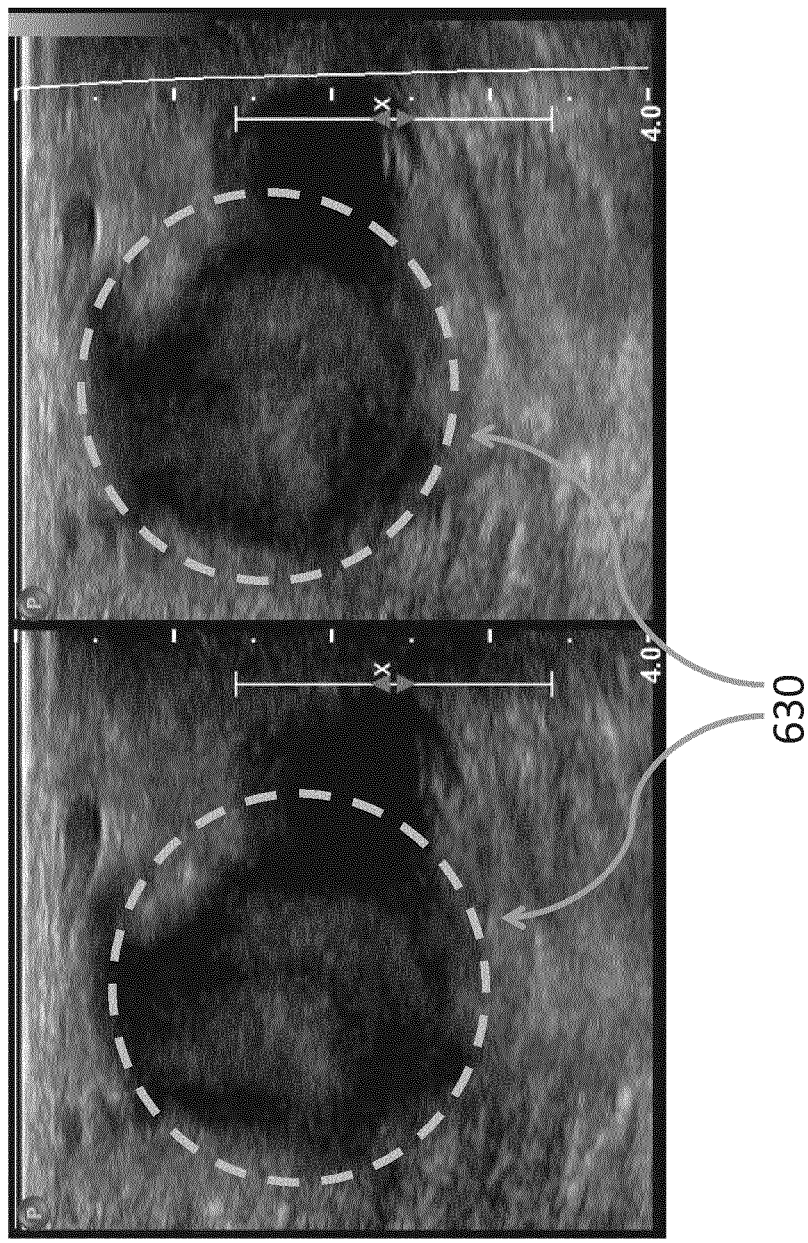
FIG. 12 is an ultrasound grey scale image of acute DVT taken using an example system, according to aspects of the present disclosure.

FIG. 12 is an ultrasound grey scale image of acute DVT taken using system 500, according to aspects of the present disclosure. Different from FIGS. 10 and 11, which are ultrasound grey scale images taken sideway from a radial direction of the vein, FIG. 12 is an ultrasound grey scale image taken along a longitudinal direction of the vein. Regions 630 in the ultrasound grey scale image shown in FIG. 12 contain airy low-intensity grey scale image signals, indicating a weak reflection of ultrasound echo from the corresponding region in the vein. The airy low-intensity grey scale image signals in regions 630 therefore indicate presence of acute blood clots.

Figure 13:
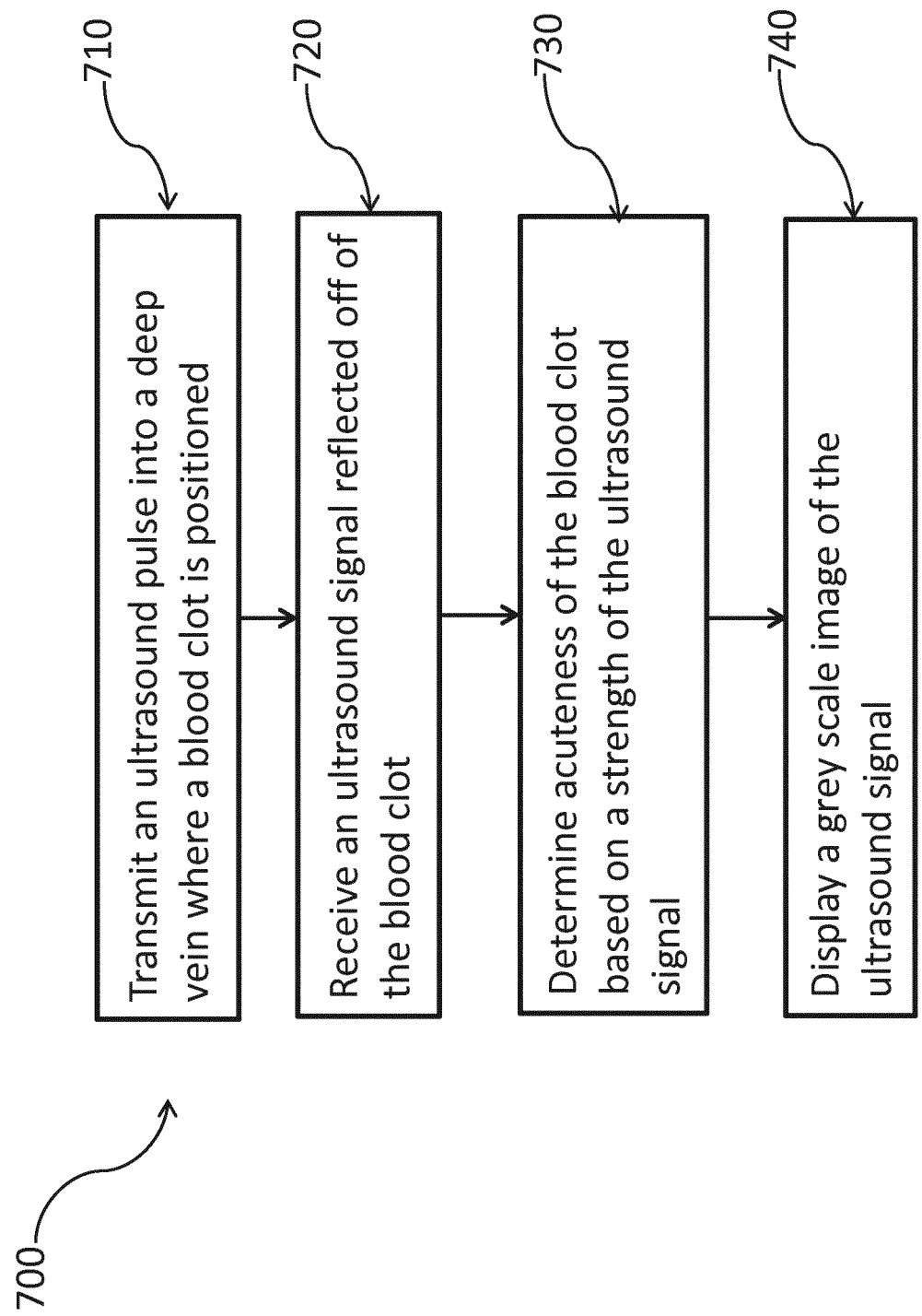
FIG. 13 is a flowchart illustrating an example method of evaluating acuteness of DVT, according to aspects of the present disclosure.

Shown in FIG. 13 is a flowchart illustrating a method 700 of determining acuteness of DVT, according to aspects of the present disclosure. At step 710, an ultrasound pulse is transmitted into a deep vein where a blood clot is positioned. Next, at step 720, an ultrasound signal representative of an ultrasound echo reflected from the blood clot is received. At step 730, the acuteness of the blood clot is determined based on the strength of the ultrasound signal representative of the ultrasound echo reflected from the blood clot. In some instances, the method 700 further includes displaying a grey scale image of the ultrasound signal.

Figure 14:
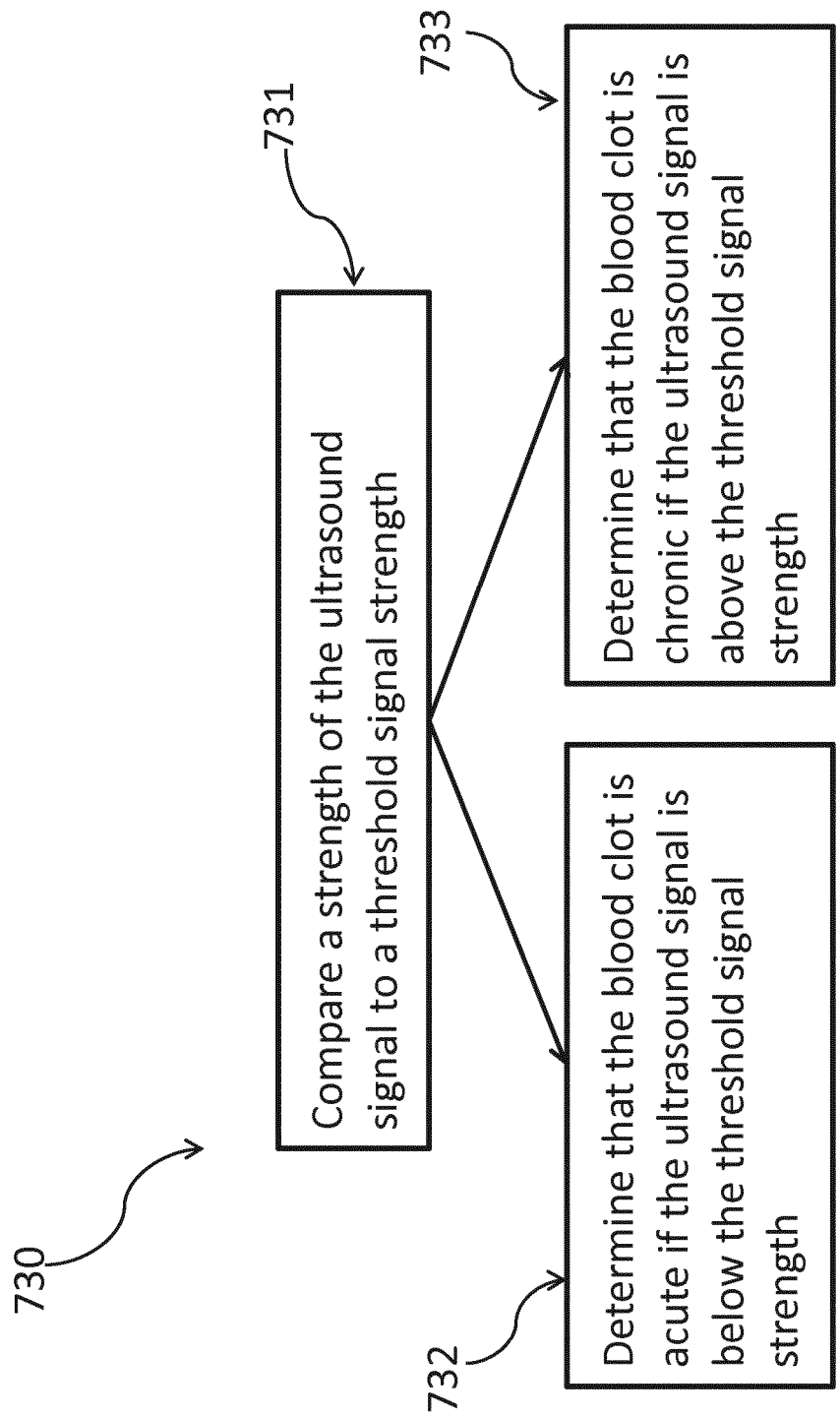
FIG. 14 is a flowchart illustrating an example method of evaluating acuteness of a blood clot based on a strength of an ultrasound signal, according to aspects of the present disclosure.

FIG. 14 is a flowchart illustrating further steps of step 730 method of determining acuteness of a blood clot based on a strength of an ultrasound signal, according to aspects of the present disclosure. At step 731, the strength of the ultrasound signal is compared to a threshold strength. If the ultrasound signal is below the threshold signal strength, then at step 732, the blood clot is determined to be acute. If the ultrasound signal is equal to or above the threshold signal strength, then at step 733, the blood clot is determined to be chronic.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for evaluating deep vein thrombosis (DVT) caused by a blood clot formed in a deep vein of a patient, the system comprising:
    an ultrasound imaging device configured to transmit an ultrasound pulse into the deep vein where the blood clot is positioned, detect an ultrasound echo reflected from the blood clot, and output an output signal representative of the ultrasound echo; and
    a processor in communication with the ultrasound imaging device, the processor operable to:
        receive the output signal representative of the ultrasound echo from the ultrasound imaging device;
        process the output signal to determine a strength of the ultrasound echo, and to display, on a display, a grey scale image of the ultrasound echo, wherein a brightness of the grey scale image is displayed in proportion to the strength of the ultrasound echo;
        compare the strength of the ultrasound signal to a threshold;
        determine an acuteness of the blood clot as acute when the strength of the ultrasound echo is below the threshold, and determine the acuteness of the blood clot as chronic when the strength of the ultrasound echo is not below the threshold; and
        output, to the display, a graphical indication of the determined acuteness,
        wherein the processor is configured such that the threshold is variably settable by a user of the ultrasound imaging device based on test results of the patient or a clinical history of the patient.

2. The system of claim 1, wherein the display displays the grey scale image of the ultrasound echo with the graphical indication of the determined acuteness comprising a first graphical overlay when the blood clot is determined as acute, and a second graphical overlay when the blood clot is determined as chronic.

3. The system of claim 2, wherein the first graphical overlay comprises a first color and the second graphical overlay comprises a second color different from the first color.

4. The system of claim 2, wherein the first graphical overlay comprises a first text and the second graphical overlay comprises a second text different from the first text.

5. The system of claim 1, wherein the ultrasound imaging device is an intravascular ultrasound catheter.

6. The system of claim 1, wherein the ultrasound imaging device is an external ultrasound probe.

7. The system of claim 1, wherein the ultrasound imaging device operates at a frequency of 10 MHz.

8. The system of claim 1, wherein the ultrasound imaging device operates at a frequency of 20 MHz.

* * * * *